United States Patent [19]

Paret

[11] Patent Number: 4,475,005
[45] Date of Patent: Oct. 2, 1984

[54] PROCESS FOR PREPARING TERTIARY ALKYL ETHERS

[75] Inventor: Giancarlo Paret, Milan, Italy

[73] Assignee: Snamprogetti S.p.A., Milan, Italy

[21] Appl. No.: 361,358

[22] Filed: Mar. 24, 1982

[30] Foreign Application Priority Data

Apr. 10, 1981 [IT] Italy .................... 21032 A/81

[51] Int. Cl.³ .............................................. C07C 41/42
[52] U.S. Cl. ..................................... 568/697; 568/699; 203/86; 203/DIG. 6
[58] Field of Search ............ 203/DIG. 6, 99, 86; 568/697, 699; 202/267

[56] References Cited

U.S. PATENT DOCUMENTS

| | | | |
|---|---|---|---|
| 2,081,322 | 5/1937 | Carney | 203/DIG. 6 X |
| 3,506,408 | 4/1970 | Kageyama et al. | 203/DIG. 6 X |
| 3,629,478 | 12/1971 | Haunschild | 568/697 X |
| 3,634,534 | 1/1972 | Haunschild | 203/DIG. 6 X |
| 4,089,752 | 5/1978 | Hancock | 203/DIG. 6 X |
| 4,232,177 | 11/1980 | Smith | 203/DIG. 6 X |
| 4,302,356 | 11/1981 | Smith | 203/DIG. 6 X |
| 4,307,254 | 12/1981 | Smith | 203/DIG. 6 X |
| 4,336,407 | 6/1982 | Smith | 203/DIG. 6 X |

Primary Examiner—Wilbur L. Bascomb, Jr.
Attorney, Agent, or Firm—Morgan, Finnegan, Pine, Foley & Lee

[57] ABSTRACT

A process for preparing tertiary alkyl ethers from isoolefins and aliphatic alcohols in the presence of a catalyst in the form of sulphonated styrene-divinylbenzene resins, characterized in that both the reaction leading to the formation of the tert-alkyl ether and the separation of the tert-alkyl ether from the hydrocarbons and compounds which accompany it take place in a single plate fractionating apparatus, in which some of the plates are provided with beds of catalyst in the form of spherules suitable for preparing said tert-alkyl ether, the ether obtained being withdrawn as a substantially pure bottom product.

8 Claims, 1 Drawing Figure

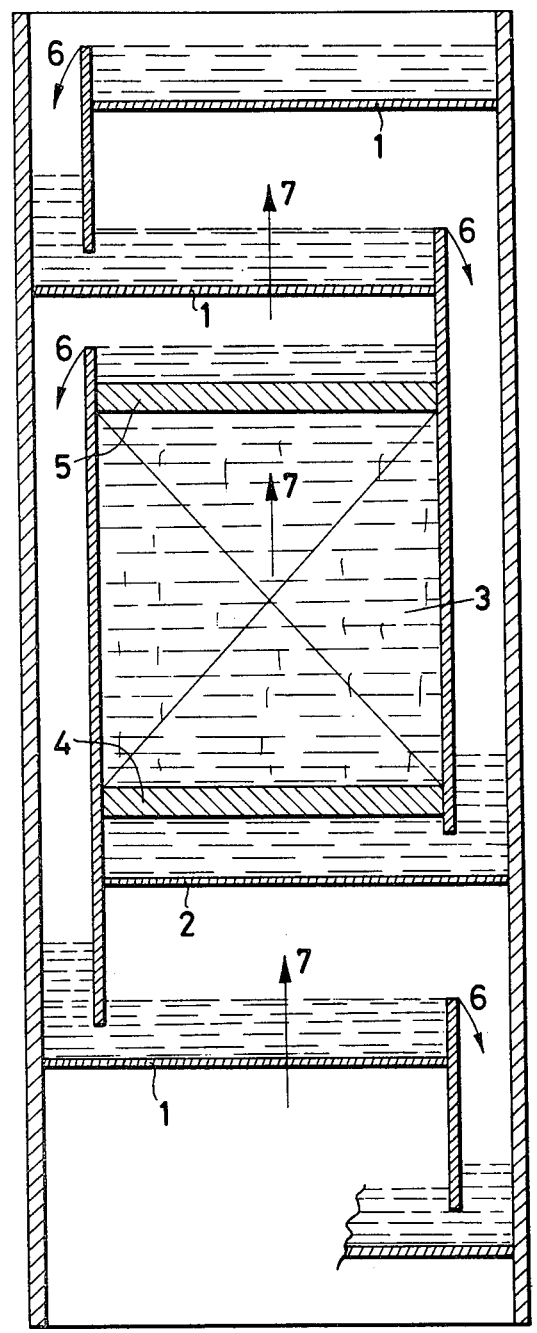

PROCESS FOR PREPARING TERTIARY ALKYL ETHERS

This invention relates to a process for preparing tertiary alkyl ethers from isoolefins and aliphatic alcohols. More particularly, the invention relates to the preparation of methyl tert-butyl ether or methyl tert-amyl ether from isobutylene and methanol, or isoamylene and methanol respectively.

In the description given hereinafter, reference will be made for reasons of simplicity to the preparation of methyl tert-butyl ether, however the process is also completely valid for the preparation of all other tert-alkyl ethers, as the differences between the boiling points of the components and products are of the same order of magnitude.

Methyl tert-butyl ether (MTBE) is prepared, according to the known art, by reacting isobutene, which is generally contained in variable percentages in a $C_4$ hydrocarbon fraction, with methanol in the presence of a suitable catalyst generally consisting of sulphonated styrene-divinylbenzene resins, at a temperature which can vary from ambient temperature to about 100° C.

In practice, isobutene is not available on a plant scale, and reference will therefore be made to the aforesaid case of the $C_4$ hydrocarbon fraction containing isobutene.

The reaction is an equilibrium reaction, and if the methanol quantity used is close to the stoichiometric, the isobutene conversion is 90% or a little more at those temperatures which give a reasonable reaction rate.

If higher conversions are required, an excess of methanol must be used, and this must then be separated from the reaction product and recycled, in which case conversions of slightly more than 95% are attained under reasonable conditions, or alternatively the reaction product must be separated and the residual mixture passed to a second reaction stage, which again under approximately stoichiometric conditions enables conversions of about 99% to be attained.

However, there is the problem that in order to carry out this operation it is necessary to evaporate the $C_4$ components twice, and use two reactors and two distillation columns so increasing the investment and running costs. The most recent art (European patent application published on Mar. 19, 1980 under No. 8860) suggests a method for overcoming the aforesaid problems, by feeding a mixture containing isobutene and methanol to a distillation column filled with catalyst suitable for the preparation of MTBE, in which the catalyst also acts as distillation packing, thus forming MTBE and separating the MTBE from the $C_4$ components at the same time.

However, the method described in the aforesaid patent application suffers from certain serious drawbacks related to the fact that the catalyst acts as the distillation column packing, and must therefore satisfy special requirements, in particular the requirement of a low pressure drop. For this reason, it is used placed in bags forming a belt, which leave ample space for the passage of the vapour and liquid, but which on the other hand are difficult to prepare and to load into the column.

The method described in the aforesaid European application also suffers from the drawback that the continuous phase inside the column is represented by the vapour phase, whereas the dispersed phase is the liquid phase, and this leads to low MTBE yields, as the reaction takes place in practice in the vapour phase.

This also leads to the possibility of the formation of substantial dimer quantities because there is an alcohol deficiency in the vapour phase.

It has now been surprisingly found possible to obviate all the aforesaid drawbacks by carrying out both the reaction leading to the formation of the tert-alkyl ether (MTBE) and its separation from the hydrocarbons and compounds which accompany it in a single plate fractionating apparatus in which some of the plates are provided with beds of catalyst in the form of spherules based on sulphonated styrene-divinylbenzene resins, suitable for the preparation of the tert-alkyl ether (MTBE).

The process according to the present invention comprises: feeding the hydrocarbon feed containing the isoolefin to a plate fractionating column in which some of the plates are provided with beds of catalyst consisting of sulphonated styrene-divinylbenzene resins and are separated from each other either by groups of fractionating plates or single fractionating plates; feeding the alcohol by itself in proximity to the top of the column, preferably above the last catalyst bed and some plates (between 4 and 8) below the point at which the reflux is fed; reacting the isoolefin with the alcohol on the plates provided with catalyst beds, which are immersed in the liquid containing the alcohol and through which the vapours bubble; and separating the produced ether from the other components at the fractionating plates and at the plates provided with catalyst beds to obtain as bottom product the substantially pure ether, and as overhead product the feed hydrocarbons and possibly the alcohol in the form of an azeotrope with the feed hydrocarbons.

The process according to the present invention in the case of MTBE comprises: feeding the $C_4$ hydrocarbon feed containing isobutene to a plate fractionating column in which some of the plates are provided with beds of catalyst consisting of sulphonated styrene-divinylbenzene resins suitable for forming MTBE and are separated from each other either by groups of fractionating plates or single fractionating plates; feeding the methanol by itself in proximity to the top of the column and preferably above the last catalyst bed and between 4 and 8 plates below the point at which the reflux is fed; reacting the isobutene with the methanol on the plates provided with catalyst beds, which are immersed in the liquid containing methanol and through which the vapour bubbles; and separating the produced MTBE from the other components both at the fractionating plates and at the plates provided with catalyst beds, to obtain as bottom product substantially pure MTBE, and as overhead product those $C_4$ hydrocarbons other than the isobutene, plus methanol in the quantity corresponding to the azeotrope.

The process according to the present invention is carried out at a pressure of between 500 and 1000 KPa.

The hydrocarbon feed containing the isoolefin is fed to the plate column according to the invention in a position such that at least two plates comprising catalyst beds are above said feed and at least one plate comprising a catalyst bed is below said feed. The vapours produced by the fractionating column reboiler bubble through the catalyst beds, which are preferably not less than three in number, and the methanol and isobutene react therein in the liquid phase which covers each catalyst bed.

The catalyst is in the form of spherules having a diameter of between 0.5 and 1 mm, and the thickness of each catalyst bed is of the order of 1 meter.

The liquid present on each plate containing the catalyst flows on to the lower distillation plate by way of one or more conventional weirs, and the catalyst always remains immersed in the liquid.

The catalyst is retained on each plate by the fact that it is contained by meshes at least at the bed base and top, which prevent it from escaping.

The invention will be more apparent from the accompanying FIGURE which illustrates a non-limiting embodiment thereof. The reference numeral 1 indicates the fractionating plates, and 2 a fractionating plate comprising thereon a catalyst bed 3, which is retained by the meshes 4 and 5.

The liquid follows the path indicated by the arrows 6, passing through the catalyst bed. The vapour follows the upward path indicated by the arrow 7. A non-limiting embodiment of the process according to the invention is described hereinafter.

EXAMPLE

A distillation column was constructed using flanged pipe sections of diameter 10 cm and length 100 cm, containing six bubble cap distillation plates (two bubble caps per plate). The column was constructed by alternating 1 m pipe sections full of catalyst with sections comprising six plates, to give a total of six sections above the feed and two sections below. The column was fed with 2 kg/h of $C_4$ containing 50% of isobutene.

A reflux ratio of 1:1 was maintained, and 575 g of methanol were fed together with the reflux. The operating pressure was 800 KPa, and the operating temperature was 60°–150° C. The overhead product consisted of 1035 g of $C_4$ containing 30 g of methanol and 5 g of isobutene.

1540 g of practically pure MTBE were obtained as bottom product.

I claim:

1. A process for reacting an isoolefin with an alkyl alcohol in the presence of a catalyst to produce the corresponding tertiary alkyl ether, said catalyst comprised of a sulphated styrene-divinylbenzene resin, said process comprising the steps of:
    a. providing a plate fractionating column reactor containing at least five fractionating reaction zones, each reaction zone being serially connected to the next successive reaction zone via a pathway which is contiguous to the reaction zones connected via said pathway, at least two of said reaction zones also containing a fixed bed of said catalyst, each of the reaction zones containing a fixed bed of said catalyst being separated from another by at least one reaction zone not containing a fixed bed of said catalyst;
    b. causing liquid in said reactor to flow along a preselected flow path in a downward direction through said reaction zones not containing a fixed bed of catalyst and through said pathways and in an upwards direction through said reaction zones containing a fixed bed of said catalyst.
    c. causing gas vapors fractioned from said liquid to flow in an upwards direction through said reaction zones;
    d. introducing said alcohol into the upper end of said column reactor into said flow path at a location above the uppermost of said reaction zones containing a fixed bed of said catalyst;
    e. introducing a hydrocarbon feed containing said isoolefin into said column reactor into said flow path;
    f. reacting said isoolefin with said alcohol in the liquid phase in each of said reaction zones containing a fixed bed of said catalyst to form said ether product, each fixed bed of said catalyst being immersed in liquid containing said alcohol, said gas vapors produced in the reaction zones located below each bed of said catalyst bubbling upwards therethrough;
    g. separating said ether product from the unreacted hydrocarbon feed in each of said fractionating reaction zones to obtain a substantially pure form of said ether product;
    h. removing said substantially pure form of said ether product from the bottom of said column reactor; and
    i. removing the unreacted hydrocarbon feed from the top of said column reactor.

2. A process as claimed in claim 1 wherein said unreacted hydrocarbon feed is refluxed into said column reactor.

3. A process as claimed in claim 2 wherein said column reactor contains at least eight reaction zones, at least two of said reaction zones containing a fixed bed of said catalyst, and wherein said alcohol is introduced into said column reactor into said flow path at a location above the uppermost located of said reaction zones containing a fixed bed of said catalyst and between four and eight reaction zones below the location at which reflux is introduced into said column reactor.

4. A process as claimed in claim 1 wherein the pressure is between about 500 and about 1,000 KPa.

5. The process as claimed in claim 1 wherein said column reactor contains at least three reaction zones containing a fixed bed of said catalyst and wherein said hydrocarbon feed containing said isoolefin is introduced into said column reactor into said flow path at a location such that at least two reaction zones containing the fixed bed of said catalyst are above said location and at least one reaction zone containing a fixed bed of said catalyst is below said location.

6. A process as claimed in claim 1 wherein said catalyst comprises spherules having a diameter of between about 0.5 and about 1 mm.

7. A process as claimed in claim 1 wherein said isoolefin is selected from isobutylene and isoamylene and said alkyl alcohol is methanol.

8. A process as claimed in claim 7 wherein the pressure is between about 500 KPa and about 1,000 KPa and the temperature is between about 60° C. and 150° C.

* * * * *